United States Patent
Kurtzberg et al.

(10) Patent No.: US 10,912,801 B2
(45) Date of Patent: Feb. 9, 2021

(54) METHODS FOR THE TREATMENT OF AUTISM SPECTRUM DISORDERS

(71) Applicant: Duke University, Durham, NC (US)

(72) Inventors: Joanne Kurtzberg, Durham, NC (US); Geraldine Dawson, Durham, NC (US); Jesse Troy, Durham, NC (US); Jessica Sun, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 16/493,754

(22) PCT Filed: Mar. 13, 2018

(86) PCT No.: PCT/US2018/022174
§ 371 (c)(1),
(2) Date: Sep. 12, 2019

(87) PCT Pub. No.: WO2018/169952
PCT Pub. Date: Sep. 20, 2018

(65) Prior Publication Data
US 2020/0069741 A1 Mar. 5, 2020

Related U.S. Application Data

(60) Provisional application No. 62/470,431, filed on Mar. 13, 2017.

(51) Int. Cl.
| | | |
|---|---|---|
| *A61K 35/14* | (2015.01) | |
| *A61K 35/51* | (2015.01) | |
| *A61B 5/16* | (2006.01) | |
| *A61P 43/00* | (2006.01) | |
| *A61B 5/0476* | (2006.01) | |
| *A61B 5/055* | (2006.01) | |
| *A61B 5/00* | (2006.01) | |
| *A61K 9/00* | (2006.01) | |

(52) U.S. Cl.
CPC ............ *A61K 35/51* (2013.01); *A61B 5/0476* (2013.01); *A61B 5/055* (2013.01); *A61B 5/163* (2017.08); *A61B 5/4848* (2013.01); *A61K 9/0019* (2013.01); *A61P 43/00* (2018.01)

(58) Field of Classification Search
CPC ..................................................... A61K 35/14
See application file for complete search history.

(56) References Cited

FOREIGN PATENT DOCUMENTS

| WO | 01/66698 A1 | 9/2001 |
| WO | 05/024064 A2 | 3/2005 |
| WO | 14/018774 A1 | 1/2014 |

OTHER PUBLICATIONS

Dawson et al., "Autologous Cord Blood Infusions are Safe and Feasible in Young Children with Autism Spectrum Disorder: Results of a Single-Center Phase I Open-Label Trial", Stem Cells Translational Medicine, 2017, 6(5), 1332-1339.

(Continued)

*Primary Examiner* — Rosanne Kosson
(74) *Attorney, Agent, or Firm* — Polsinelli PC; Michelle L. McMullen; J. Wendy Davis (57) ABSTRACT

The present disclosure provides methods for the treatment of autism spectrum disorders. More particularly, the present disclosure relates to methods of using cord blood for the treatment of autism spectrum disorders.

15 Claims, 4 Drawing Sheets

(56) References Cited

OTHER PUBLICATIONS

Chawarska K, et al., J Child Psychol Psychiatry, (2012), "Context modulates attention to social scenes in toddlers with autism", vol. 53, pp. 903-913.
MMWR Surveill Summ (2014), "Prevalence of Autism Spectrum Disorder Among Children Aged 8 Years—Autism and Developmental Disabilities Monitoring Network, 11 Sites, United States, 2010", vol. 63, pp. 1-21.
Buescher AS, et al., JAMA Pediatrics, "Costs of Autism Spectrum Disorders in the United Kingdom and the United States", (2014), vol. 168, pp. 721-728.
Dawson G, et al., Pediatrics, (2010), "Randomized, Controlled Trial of an Intervention for Toddlers With Autism: The Early Start Denver Model", vol. 125, pp. e17-e23.
De la Torre-Ubieta L, et al., Nat Med, (2016), "Advancing the understanding of autism disease mechanisms through genetics", vol. 22, pp. 345-361.
Mandy W, Lai MC., J. Child Psychol Psychiatry, (2016), "Annual Research Review: The role of the environment in the developmental psychopathology of autism spectrum condition", vol. 57, pp. 271-292.
Sahin M, sur M. Science, (2015), "Genes, circuits, and precision therapies for autism and related neurodevelopmental disorders", vol. 350, Issue 6263, pp. aab3897-1-aab3897-8.
Gao R, Penzes P., Curr Mol Med, (2015), "Common Mechanisms of Excitatory and Inhibitory Imbalance in Schizophrenia and Autism Spectrum Disorders", vol. 15, pp. 146-167.
Volk L, et al., Annu Rev Neurosci, (2015), "Glutamate Synapses in Human Cognitive Disorders", vol. 38, pp. 127-149.
Wolff JJ, et al., Am J. Psychiatry, (2012), "Differences in White Matter Fiber Tract Development Present From 6 to 24 Months in Infants With Autism", vol. 169, pp. 589-600.
Young AMH, et al., Mol Autism, (2016), "REVIEW Open Access From molecules to neural morphology: understanding neuroinflammation in autism spectrum condition", vol. 7, pp. 1-8.
Voineagu I, et al., Nature, (2011), "Transcriptomic analysis of autistic brain reveals convergent molecular pathology", vol. 474, pp. 380-384.
Braunschweig D, et al., Transl Psychiatry, (2013), "Autism-specific maternal autoantibodies recognize critical proteins in developing brain", vol. 3, pp. e277.
Vargas DL, et al., Ann Neurol, (2005), "Neuroglial Activation and Neuroinflammation in the Brain of Patients with Autism", vol. 57, pp. 67-81.
Morgan JT, et al., Biol Psychiatry, (2010), "Microglial Activation and Increased Microglial Density Observed in the Dorsolateral Prefrontal Cortex in Autism", vol. 68, pp. 368-376.
Suzuki K, et al., JAMA Psychiatry, (2013), "Microglial Activation in Young Adults With Autism Spectrum Disorder", vol. 10, pp. 49-58.
Bachstetter AD, et al., BMC Neurosci, (2008), "Peripheral injection of human umbilical cord blood stimulates neurogenesis in the aged rat brain", vol. 9, pp. 22.
Shahaduzzaman M, et al., Age (Dordr), (2013), "A single administration of human umbilical cord blood T cells produces long-lasting effects in the aging hippocampus", vol. 35, pp. 2071-2087.
Sun J, et al., Transfusion, (2010), "Differences in quality between privately and publicly banked umbilical cord blood units: a pilot study of autologous cord blood infusion in children with acquired neurologic disorders", vol. 50, pp. 1980-1987.
Cotton CM, et al., J. Pediatr, (2014), "Feasibility of Autologous Cord Blood Cells for Infants with Hypoxic-Ischemic Encephalopathy", vol. 164, pp. 973-979.
Sun J, et al, Pediatr Res, (2015), "Repeated autologous umbilical cord blood infusions are feasible and had no acute safety issues in young babies with congenital hydrocephalus", vol. 78, pp. 712-716.
Shoulars K, et al., Blood, (2016), "Development and validation of a rapid, aldehyde dehydrogenase bright—based cord blood potency assay", vol. 12, pp. 2346-2354.
Rubinstein P, et al., Proc. Natl. Acad Sci USA, (1995), "Processing and cryopreservation of placental/umbilical cord blood for unrelated bone marrow reconstitution", vol. 92, pp. 10119-10122.
Balboni G, et al., J. Autism Dev. Disord, (2016), "The Vineland-II in Preschool Children with Autism Spectrum Disorders: An Item Content Category Analysis", vol. 46, pp. 42-52.
Perry A, et al., J. Autism Dev. Disord, (2009), "Brief Report: The Vineland Adaptive Behavior Scales in Young Children with Autism Spectrum Disorders at Different Cognitive Levels", vol. 39, pp. 1066-1078.
Yang S, et al., J. Autism Dev. Disord, (2016), Vineland Adaptive Behavior Scales: II Profile of Young Children with Autism Spectrum Disorder, vol. 46, pp. 64-73.
ClinicalTrials.gov listing. Autologous Cord Blood Stem Cells for Autism.†
Lv, Y., Zhang, Y., Liu, M. et al. Transplantation of human cord Blood mononuclear cells and umbilical cord-derived mesenchymal stem cells in autism, J Transl Med 2013. 11, 196 to 206.†

† cited by third party

METHODS FOR THE TREATMENT OF AUTISM SPECTRUM DISORDERS

CROSS-REFERENCE TO RELATED APPLICATIONS

This application is the US national phase under 35 U.S.C. § 371 of International Application No. PCT/US2018/022174, filed Mar. 13 2018, which claims the benefit of U.S. Provisional Patent Application No. 62/470,431, filed Mar. 13, 2017, the contents of each of which are incorporated herein by reference in their entirety.

BACKGROUND OF THE INVENTION

Field of the Invention

The present disclosure provides methods for the treatment of Autism Spectrum Disorder. More particularly, the present disclosure relates to methods of using cord blood to treat Autism Spectrum Disorder.

Description of the Related Art

Autism, or autism spectrum disorder (ASD), refers to a range of conditions characterized by challenges with social skills, repetitive behaviors, speech and nonverbal communication, as well as by impairments in social communication and the presence of repetitive and restricted range of activities, with onset early in life. ASD is a clinical diagnosis based on the presence of specific behavioral symptoms, which can be caused by different combinations of genetic and environmental influences. The term "spectrum" reflects the wide variation in challenges and strengths possessed by each person with autism.

The Centers for Disease Control and Prevention (CDC) estimates prevalence of ASD to be 1 in 68 children in the United States (MMWR Surveill Summ 2014; 63:1-21). This includes 1 in 42 boys and 1 in 189 girls. The majority of individuals with ASD are not able to live independently and require lifelong support or accommodations. Accordingly, the lifetime cost of supporting an individual with ASD is estimated to be $1.4 million. The estimated cost rises to $2.4 million for those who also have an intellectual disability. (Buescher A S, et al. *JAMA Pediatrics* 2014; 168:721-728). An estimated 50,000 teens with autism become adults—and lose school-based autism services—each year. Around one third of people with autism remain nonverbal. Around forty percent of people with autism have an intellectual disability. Certain medical and mental health issues frequently accompany autism. They include gastrointestinal (GI) disorders, seizures, sleep disturbances, attention deficit and hyperactivity disorder (ADHD), anxiety and phobias. Current treatment approaches for ASD include medication, behavioral therapy, occupational and speech therapies, and specialized educational and vocational support. Early intensive behavioral intervention is associated with substantially improved outcomes (Dawson G, et al. *Pediatrics* 2010; 125:e17-e23), but even with such intervention, many individuals with ASD remain significantly impaired. While current treatments are supportive, they focus on managing sequelae with physical therapies, medications, and surgery. Currently available medical treatments, such as psychotropic medications, are intended to ameliorate associated co-morbid symptoms, such as irritability, but do not address core ASD symptoms. In light of this, there is a large unmet need for novel, effective treatments targeting core symptoms of ASD.

Both genetic and environmental factors contribute to the etiology of ASD (de la Torre-Ubieta L, et al. *Nat Med* 2016; 22:345-361; Mandy W, Lai M C. *J. Child Psychol Psychiatry* 2016; 57:271-292; Sahin M, *Sur M. Science* 2015; 350). Although the exact pathophysiology is unknown, observations have included abnormal synaptic functioning in areas of the brain (Gao R, Penzes P. *Curr Mol Med* 2015; 15:146-167; Volk L, et al. *Annu Rev Neurosci* 2015; 38:127-149), white matter abnormalities (Wolff J J, et al. *Am J Psychiatry* 2012; 169:589-600), and neuroinflammation (Young A M H, et al. *Mol Autism* 2016; 7:1-8). Pathogenesis of immune pathology in the brains of patients with ASD may be due to overexpression of immune-related gene networks (Voineagu I, et al. *Nature* 2011; 474:380-384), presence of maternal antibodies to fetal brain tissue (Braunschweig D, et al. *Transl Psychiatry* 2013; 3:e277), atypical levels of proinflammatory cytokines (IL-6, TNF-α) in the cerebral spinal fluid (Vargas D L, et al. *Ann Neurol* 2005; 57:67-81), and excessive microglial activation leading to aberrant neural connectivity pathways (Morgan J T, et al. *Biol Psychiatry* 2010; 68:368-376; Suzuki K, et al. *JAMA Psychiatry* 2013; 70:49-58). As such, therapeutic approaches impacting immune modulation or regulation of neural connectivity are logical targets for novel treatments for this population. Preclinical models have shown that umbilical cord blood contains effector cells that, through paracrine signaling, alter brain connectivity and also work to suppress inflammation (Bachstetter A D, et al. *BMC Neurosci* 2008; 9:22; Shahaduzzaman M, et al. *Age (Dordr)* 2013; 35:2071-2087). Infusions of autologous cord blood cells have been shown to be safe in patients with cerebral palsy and other acquired brain injuries (Sun J, et al. *Transfusion* 2010; 50:1980-1987; Cotton C M, et al. *J Pediatr* 2014; 164:973-979; Sun J M, et al. *Pediatr Res* 2015; 78:712-716).

Microglia play critical but incompletely understood roles in propagation and resolution of central nervous system (CNS) damage. These cells modulate neuroinflammation, produce factors that regulate activities of astrocytes, oligodendrocytes, and neurons, and clear debris to provide an environment for oligodendrocytes to begin to remyelinate neurons. In mice, microglia arise from a unique pool of replicating precursors in the brain that is originally derived from the extraembryonic yolk sac early in fetal development. Bone marrow-derived, circulating blood monocytes constitute another potential source of infiltrating phagocytic cells that can exacerbate or ameliorate CNS damage. Although a pathway for circulation of monocytes between lymph and brain parenchyma has recently been described, large numbers of circulating monocytes do not enter the uninjured, adult mouse brain but may infiltrate the CNS following insult such as brain irradiation, chemotherapy or injury, demyelinating conditions, or chronic stress. In some models, these infiltrating blood monocytes may activate inflammation and participate in demyelinating events. In others, blood monocytes may facilitate remyelination.

Despite advances in early diagnosis and behavioral therapies, more effective treatments for children with ASD are needed. Umbilical cord blood-derived cell therapies may have potential in alleviating ASD symptoms by modulating inflammatory processes in the brain.

SUMMARY OF THE INVENTION

One aspect of the present disclosure provides methods of treating a patient suffering from an autism spectrum disorder. Such methods include administering to the patient a therapeutically effective amount of cord blood such that the disease is treated.

Another aspect of the present disclosure provides methods of assessing the therapeutic effectiveness of cord blood treatment on a patient suffering from an autism spectrum disorder. Such methods include (a) performing one or more appropriate tests on the patient to establish behavioral and biomarker baseline score(s); (b) administering an effective amount of cord blood to the patient; (c) reevaluating the patient at one or more time points post-administration of cord blood for the same one or more behavioral and biomarker tests set forth in (a); and (d) comparing the results in (c) with the baseline score(s) established in (a).

BRIEF DESCRIPTION OF THE DRAWINGS

The accompanying drawings are included to provide a further understanding of the methods of the disclosure, and are incorporated in and constitute a part of this specification. The drawings illustrate one or more embodiment(s) of the disclosure, and together with the description serve to explain the principles and operation of the disclosure.

FIG. 2 illustrates the VABS-II socialization standard score. (A) shows the distribution of VABS-II Socialization standard scores in all participants over time. A statistically significant increase in standard score was observed from baseline to 6 months. This change was stable from 6-12 months. (B) shows the distribution of VABS-II Socialization score stratified by non-verbal IQ (NVIQ). Individuals with a NVIQ<70 (N=12) are shown together, depicted with a circle (○); individuals with a NVIQ>70 (N-12) are shown together, depicted with a plus (+). The change in 2A is positively correlated in 2B with nonverbal IQ in the Socialization ($r_s$=0.57, 95% CI: 0.20-0.79, P=0.004) and Adaptive Behavior ($r_s$=0.42, 95% CI: 0.01-0.70, P=0.04) domains, but not in the Communication domain ($r_s$=0.22, 95% CI: −0.21-0.57, P=0.31). Both the VABS-II Socialization domain standard scores and those stratified by NVIQ were determined for all participants (n=24) who completed the assessments at all three time points: Baseline (just prior to cord blood infusion), 6 months and 12 months post-infusion.

FIG. 3 illustrates the severity and change in severity of the core symptoms of ASD through CGI-S and CGI-I clinician-rated measures. (A) shows distribution of CGI-S severity over time in 22 participants fully evaluated at each time point: baseline (just prior to cord blood infusion), 6 months and 12 months post-infusion. (B) shows the distribution of CGI-I in the same 22 participants at 6 and 12 months post-infusion. Improvement measured at each time point is related to baseline. CGI-I at 12 months post-infusion was associated with nonverbal IQ, but not age or infused cell dose (not shown).

DETAILED DESCRIPTION OF THE INVENTION

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

It is also to be understood that unless clearly indicated otherwise by the context, embodiments disclosed for one aspect or embodiment of the invention can be used in other aspects or embodiments of the invention as well, and/or in combination with embodiments disclosed in the same or other aspects of the invention. Thus, the disclosure is intended to include, and the invention includes, such combinations, even where such combinations have not been explicitly delineated.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

As used herein, "treatment," "therapy" and/or "therapy regimen" refer to the clinical intervention made in response to a disease, disorder or physiological condition (e.g., autism spectrum disorder) manifested by a patient or to which a patient may be susceptible. The aim of treatment includes the alleviation or prevention of symptoms, slowing or stopping the progression or worsening of a disease, disorder, or condition and/or the remission of the disease, disorder or condition (e.g., autism spectrum disorder).

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that has, or suffers from, an autism spectrum disorder.

As used herein, the terms "autism spectrum disorder" and "autism" are used interchangeably and refer to any range of mental conditions, generally present from early childhood, that are characterized by difficulty in communicating and forming relationships with other people and in using language and abstract concepts.

Treatment of Autism Spectrum Disorder by Cord Blood or Cord Blood Components

In view of the present disclosure, the methods described herein can be configured by the person of ordinary skill in the art to meet the desired need. In general, the disclosed materials, methods, and apparati provide methods of treating a subject suffering from an autism spectrum disorder comprising, consisting of, or consisting essentially of administering to the subject a therapeutically effective amount of cord blood and/or a component or mixture of components thereof, such that the autism spectrum disorder is treated.

It is to be understood that as used herein, unless stated otherwise, the term "cord blood" is meant to encompass cord blood in any format and/or a component or mixture of components thereof, whether specifically so stated or not.

In some embodiments, the cord blood is autologous, i.e. the patient's own cord blood.

The patient may be any human or nonhuman animal. In one embodiment, the patient is human. In another embodiment, the patient is a human child under 18 years of age, or in any age range falling within this broader age range. In non-limiting examples, the patient may be 1 year to 10 years old, 1 year to 8 years old, 1 year to 6 years old, 1 year to 4 years old, 2 years to 10 years old, 2 years to 8 years old, 2 years to 6 years old, 2 years to 4 years old, 3 years to 10 years old, 3 years to 8 years old, 3 years to 6 years old, 4 years to 10 years old, 4 years to 8 years old, or 4 years to 6 years old.

The cord blood can be preserved and prepared for administration by methods known in the art. The cord blood may be administered to a subject by any technique known in the art, including systemic delivery. Routes of administration include, but are not limited to, intravenous administration. In some embodiments, the cord blood is administered systemically. In further embodiments, the cord blood is administered by intravenous (IV) injection.

We hypothesized that infusions of autologous cord blood cells could play an important role in the treatment of ASD and conducted a single center, open-labelled, phase I safety and feasibility trial in young pediatric participants. The study focused on (1) the safety of a single intravenous infusion of autologous umbilical cord blood and (2) the sensitivity to change and feasibility of administration of several different assessment tools in young children with ASD. Twenty-five (25) children with a median age of 4.6 years (range 2.26-5.97), with a confirmed diagnosis of ASD and a qualified banked autologous umbilical cord blood unit were enrolled. Children were evaluated with a battery of behavioral and functional tests immediately prior to the cord blood infusion (baseline) and 6 and 12 months later. Assessment of adverse events across the 12-month period indicated that the treatment was safe and well tolerated. Significant improvements in children's behavior were observed on parent-report measures of social communication skills and autism symptoms, clinician ratings of overall autism symptom severity and degree of improvement, standardized measures of expressive vocabulary, and objective eye-tracking measures of children's attention to social stimuli, indicating that these measures may be useful endpoints in future studies. Behavioral improvements were observed during the first 6 months after infusion and were greater in children with higher baseline nonverbal IQs.

Administration of Cord Blood

The route of administration of the cord blood may be selected by one of skill in the art based on the diseases treated and desired results. Thus, in certain embodiments, the cord blood is administered via peripheral intravenous (IV) infusion.

The cord blood of the disclosure may be administered in a single dose. The cord blood of the disclosure may also be administered in multiple doses (e.g., two, three, or more single doses per treatment) over a time period (e.g., hours, or days, or months). In certain embodiments, the cord blood of the disclosure may be administered over a time period in the range of about 1 minute to about 60 minutes, e.g., about 60 seconds to about 120 seconds, or over about 90 seconds to about 120 seconds, or over about 60 seconds to about 180 seconds, over about 90 seconds to about 180 seconds, or over about 2 minutes to about 60 minutes, or over about 2 minutes to about 50 minutes, or over about 2 minutes to about 40 minutes, or over about 2 minutes to about 30 minutes, or over about 2 minutes to about 20 minutes, or over about 2 minutes to about 10 minutes, or over about 2 minutes to about 5 minutes, or over about 10 minutes to about 60 minutes, or over about 10 minutes to about 50 minutes, or over about 10 minutes to about 40 minutes, or over about 10 minutes to about 30 minutes, or over about 10 minutes to about 20 minutes.

The cord blood cells may be present in a therapeutically effective concentration. In certain embodiments, the concentration of cord blood cells is about $1 \times 10^7$ to about $5 \times 10^8$ cells/kg body weight at the time of administration; e.g., about $1 \times 10^7$ to about $3 \times 10^8$ cells/kg, or about $1 \times 10^7$ to about $2.5 \times 10^8$ cells/kg, or about $2 \times 10^7$ to about $3 \times 10^8$ cells/kg, about $2 \times 10^7$ to about $2.5 \times 10^8$ cells/kg, or about $2 \times 10^7$ to about $2 \times 10^8$ cells/kg, or about $2.5 \times 10^7$ to about $3 \times 10^8$ cells/kg, or about $2.5 \times 10^7$ to about $2 \times 10^8$ cells/kg. One of skill in the art will recognize that suitable volume of the dose may be selected based on the desired route of administration. For example, intravenous administration may use dose volumes in the range of about 10 mL to about 50 mL; e.g., about 10 mL to about 40 mL, or about 10 mL to about 30 mL, or about 10 mL to about 20 mL, or about 10 mL to about 15 mL, or about 20 mL to about 50 mL, or about 20 mL to about 40 mL, or about 20 mL to about 30 mL, or about 30 mL to about 50 mL, or about 30 mL to about 40 mL, or about 40 mL to about 50 mL.

In certain embodiments where peripheral IV administration is used, IV fluids may be administered at about 1.0 to about 2.0 times maintenance. For example, IV fluids may be administered post-infusion at about or 1.0 to about 1.5 times maintenance, or about 1.5 to about 2.0 times maintenance. The maintenance IV fluids may be administered for about 20 minutes to about 3 hours after the cord blood infusion. For example, maintenance IV fluids may be administered post-infusion for, e.g., about 30 minutes to about 3 hours, or about 30 minutes to about 2.5 hours, or about 30 minutes to about 2 hours, or about 30 minutes to about 1.5 hours, or about 30 minutes to about 1 hour, or about 30 minutes to about 45 minutes, or about 1 hour to about 3 hours, or about 1 hour to about 2.5 hours, or about 1 hour to about 2 hours, or about 1 hour to about 1.5 hours.

Any suitable intravenous fluids may be used for maintenance post cord blood infusion. In certain embodiments, the maintenance IV fluid is a saline solution or Ringer's lactate solution. In certain embodiments, the maintenance IV fluid is 0.25% normal saline solution. In certain embodiments, the maintenance IV fluid is 0.5% normal saline solution.

Multiple assessments were utilized to determine both feasibility of administration and utility as an endpoint for future phase II and III clinical trials. These assessments or tests included both behavioral and biomarker tests. In some embodiments, behavioral tests performed or administered include but are not limited to, the Vineland Adaptive Behavior Scales-II (VABS-II), Clinical Global Impression Scale (CGI), Pervasive Developmental Disorder Behavior Inventory (PDDBI), Expressive One-Word Picture Vocabulary Test-4 (EOWPVT-4), Behavior Assessment for Children- Social Skills subscale, Aberrant Behavior Checklist, Sensory Experiences Questionnaire, Repetitive Behavior Scale, Intelligence Scales (Mullen Scales of Early Learning or Stanford-Binet), Language Environment Analysis, Preschool Age Psychiatric Assessment, Aberrant Behavior Checklist, ATN GI Symptoms Inventory, and Parenting Stress Index. In some embodiments, objective biomarker tests administered include, but are not limited to, Eye Gaze Tracking of Social Stimuli (EGT), Electroencephalogram (EEG), and brain Magnetic Resonance Imaging (MRI).

In some embodiments, one or more of the behavioral tests and objective biomarker tests are performed on a patient with ASD prior to administering an effective amount of cord blood, to establish baseline behavioral and biomarker scores. In some embodiments, the patient is reevaluated post-administration of an effective amount of cord blood for the same one or more behavioral tests and objective biomarker tests. In some embodiments, the results of the tests performed post-administration of the cord blood are compared with the baseline results of the same tests performed prior to administration of the cord blood. In some embodiments, the VABS-II Socialization Subscale Standard Score is the primary behavioral endpoint. In some embodiments, CGI, PDDBI and EOWPVT are key secondary behavioral endpoints. In some embodiments, the objective biomarker test is EGT.

In some embodiments, the patient is reevaluated at one or more time points post-administration of an effective amount of cord blood, including, but not limited to, 3 months, 6 months, 9 months, 12 months, 18 months, and 24 months post-administration of the cord blood. In some embodiments, the patient is reevaluated at 3 months post-administration of an effective amount of cord blood. In some embodiments, the patient is reevaluated at 6 months post-administration of an effective amount of cord blood. In some embodiments, the patient is reevaluated at 9 months post-administration of an effective amount of cord blood. In some embodiments, the patient is reevaluated at 12 months post-administration of an effective amount of cord blood. In some embodiments, the patient is reevaluated at 18 months post-administration of an effective amount of cord blood. In some embodiments, the patient is reevaluated at 24 months post-administration of an effective amount of cord blood. In some embodiments, the patient is revaluated at 3 months, 6 months, 9 months and 12 months post-administration of an effective amount of cord blood.

Certain aspects of the disclosure are now explained further via the following non-limiting examples.

EXAMPLES

Example 1: Cord Blood Infusions are Safe and Feasible in Young Children with Autism Spectrum Disorder Materials and Methods
Study Design and Overview A phase I, single-center, open-label trial of a single intravenous infusion of autologous umbilical cord blood was performed on 25 children with ASD. All children were initially enrolled on a screening protocol to obtain medical records and information about each child's banked cord blood unit. All participants' caregivers completed a pre-study screening interview by phone and provided medical records and videos for review by the study team to determine eligibility for the trial. Children with a confirmed diagnosis of ASD and a qualified banked autologous umbilical were eligible to participate. Written informed consent was obtained for both the screening and the treatment phases of the trial. The trial was approved by the Duke Hospital Institutional Review Board conducted under IND #15949.

Participants and their caregivers travelled to Duke University three times a part of their participation in the study. At their baseline visit, each participant was evaluated and received a single intravenous autologous cord blood infusion. At six (6) and 12 months post-infusion, participants returned for follow-up clinical assessments. Additional caregiver interviews and questionnaires were collected at 3 and 9 months post-infusion.

Participants

Participants between 2 and 5 years of age who met criteria for a clinical diagnosis of ASD based on the Diagnostic and Statistical Manual of Mental Disorders, Fifth Edition (DSM-5) (DSM-5. American Psychiatric Association 2013; Washington, D.C.) were eligible for inclusion in the study. The DSM-5 diagnosis of ASD was established by expert clinicians and informed by the Autism Diagnostic Observation Schedule, Second Edition (ADOS-2) (Lord C, et al. ADOS-2. Torrence, Calif. Western Psychological Services 2012) and the Autism Diagnostic interview, Revised (ADI-R) (Rutter M, et al. ADI-R. Torrence, Calif. Western Psychological Services 2005). Additional inclusion criteria included (1) a non-verbal intelligence quotient (IQ) of ≥35 on the Stanford-Binet Intelligence Scales for Early Childhood, Fifth Edition (Roid G H. SB5. Itasca, Ill. Riverside Publishing 2003) or Mullen Scales of Early Learning, (Mullen E. AGS ed. Bloomington, Minn. NCS Pearson Inc. 1995) (2) availability of a qualified autologous umbilical cord blood unit, (3) participant was stable on their current medications for at least 2 months prior to the infusion, (4) ability to travel to Duke University three times (baseline and 6 and 12 months post-baseline), and (5) parents were English speaking. Exclusion criteria included (1) a history of prior cell therapy, (2) use of intravenous immunoglobulin (IVIG) or other anti-inflammatory medications (with the exception of NSAIDs), (3) known genetic (e.g., fragile X) or other significant medical comorbidity, (4) obvious physical dysmorphology suggestive of a genetic syndrome, (5) an uncontrolled seizure disorder, (6) significantly impaired renal or liver function, and (7) clinically significant abnormalities in complete blood count (CBC).

Umbilical Cord Blood Units

All participants were required to have an available autologous umbilical cord blood unit banked at a family or public cord blood bank. During screening, potential participants' cord blood reports were reviewed to ensure they met the following pre-cryopreservation criteria: (1) total nucleated cell count (TNCC)≥$1 \times 10^7$/kg, (2) sterility cultures which were performed and negative, (3) negative maternal infectious disease markers tested on the maternal donor or cord blood product (minimally including hepatitis B, hepatitis C, human immunodeficiency virus (HIV), human T-lymphotrophic virus (HTLV), and syphilis), and (4) test sample available for additional testing to confirm identity and potency. If the participant and their cord blood unit were likely to be eligible, a sample of the cord blood unit was shipped to Duke for potency testing. (Shoulars K, et al. *Blood* 2016; 12:2346-2354). Low-resolution Human Leukocyte Antigen (HLA) testing was performed on both the participant and a sample of the cord blood unit for identity confirmation. If CD45 viability on the test sample was >40% and HLA-identity was confirmed, the cryopreserved cord blood unit was shipped in a dry shipper to Duke Stem cell Transplant Laboratory, where it was stored under liquid nitrogen until the day of infusion.

Procedures: Autologous Umbilical Cord Blood Infusion

On the day of infusion, the cord blood was thawed and washed in dextran 40+5% albumin (DA) and placed in 1.25 mL/kg DA for administration (Rubinstein P, et al. *Proc Natl Acad Sci USA* 1995; 92:10119-10122). Thawed CBUs were tested for enumeration of TNCC, viable CD34+ cells, colony forming units (CFUs), cell viability via trypan blue, and sterility cultures. The autologous umbilical cord blood infusion was performed following a sedated brain MRI. Intravenous (IV) access was obtained by a pediatric anesthesiologist. When the MRI was complete, children were admitted to the Duke Children's Health Center Day Hospital, an outpatient treatment center, for their infusion. After premedication with Benadryl (0.5 mg/kg IV), Solumedrol (0.5 mg/kg IV), and, if the child was awake and able to take oral medications, Tylenol (10 mg/kg PO), participants received either a portion of or their entire cord blood unit, adjusted to deliver $1\text{-}5\times10^7$ cells/kg, via peripheral IV infusion over two to thirty minutes. Intravenous fluids were administered at 1.5 times maintenance for 30 minutes to two hours after the cord blood infusion. Vital signs and pulse oximetry were monitored continuously during the infusion and until the child awoke from sedation.

Safety Evaluation Criteria

Participants were observed during the infusion and monitored for infusion reactions. Additional Adverse Events (AE) were identified through phone interviews with participants' parent/guardian at 7-10 days, 3 months, and 9 months after infusion, and in person at the baseline, 6- and 12-month clinic visits. For analysis, verbatim AE terms were mapped onto standard terminology defined by the Common Terminology Criteria for Adverse Events (CTCAE) version 4.0 and summarized according to severity and relationship to the intervention as judged by the investigator.

Clinical Assessments

Multiple assessments were utilized to determine both feasibility of administration and utility as an endpoint for future phase II and III clinical trials. These included the Vineland Adaptive Behavior Scales-II (VABS-II), Clinical Global Impression Scale (CGI), Pervasive Developmental Disorder Behavior Inventory (PDDBI), Expressive One-Word Picture Vocabulary Test-4 (EOWPVT-4), Behavior Assessment for Children-Social Skills subscale, Aberrant Behavior Checklist, Sensory Experiences Questionnaire, Repetitive Behavior Scale, Intelligence Scales (Mullen Scales of Early Learning or Stanford-Binet), Language Environment Analysis, Preschool Age Psychiatric Assessment, Aberrant Behavior Checklist, ATN GI Symptoms Inventory, and Parenting Stress Index. In addition, three objective biomarkers were collected: Eye Gaze Tracking of Social Stimuli (EGT), EEG, and brain MRI. EEG and brain MRI findings will be reported separately. Outcomes of measures that were chosen a priori as a primary behavioral endpoint (VABS-II Socialization Subscale Standard Score) and as key secondary behavioral endpoints (CGI, PDDBI, EOWPVT) and of the EGT biomarker are included in this report.

The Vineland Adaptive Behavior Scales-II (VABS-II) (Sparrow S, et al. Vineland II: 2nd ed. Minneapolis, Minn. NCS Pearson Inc; 2005) is a caregiver questionnaire that is used to assess children's adaptive behavior across a wide range of domains. The VABS-II is a well-standardized measure with strong reliability and validity (Balboni G, et al. *J Autism Dev Disord* 2016; 46:42-52; Perry A, et al. *J Autism Dev Disord* 2009; 39:1066-1078; Yang S, et al. *J Autism Dev Disord* 2016; 46:64-73; Sparrow S, et al. Vineland Survey Forms Manual. 2nd ed. Minneapolis, Minn.; NCS Pearson Inc; 2005) which yields an overall composite score, as well as subscale standard scores in the following domains: Socialization, Communication, Daily Living Skills, and Motor Skills. The VABS-II was collected from each participant's primary caregiver at the baseline and 6- and 12-month visits. The Socialization Subscale Score was used to measure improvements in the core ASD symptom of social behavior.

The Clinical Global Impression (CGI) is a commonly used rating scale that measures symptom severity and treatment response or change in behavior between time points. Two versions of the CGI were used: CGI-Severity (CGI-S) and CGI-Improvement (CGI-I). The CGI-S is a 7-point scale indicating the severity of each participant's symptoms of ASD at the time of assessment, relative to the expert rater's past experience with participants who have the same diagnosis. Based on the expert rater's lifetime clinical experience and all available information, each participant was rated as 1: not present (no ASD), 2: ASD symptoms barely evident, 3: mild ASD symptoms, 4: moderate ASD symptoms, 5: moderately severe ASD symptoms, 6: severe ASD symptoms, or 7: very severe ASD symptoms. Each participant was assigned a CGI-S rating at the baseline and 6 and 12 month visits. The CGI-I is a 7-point scale indicating the degree of improvement or worsening of ASD symptoms relative to baseline. Based on all available information, each participant was rated as 1: very much improved, 2: much improved, 3: minimally improved, 4: no change, 5: minimally worse, 6: much worse, or 7: very much worse. Each participant was assigned a CGI-I rating at the 6- and 12-month visits, and each referenced the degree of improvement or worsening relative to baseline. All CGI-S and CGI-I ratings were made by highly experienced clinicians with expertise in ASD.

The Pervasive Developmental Disorder Behavior inventory (PDDBI) (Cohen I L, Sudhalter V. PDDBI. Lutz, Fla. Psychological Assessment Resources Inc; 2005) is a caregiver questionnaire that is designed to measure social behavior, adaptive functioning, and maladaptive functioning in areas typically affected by ASD. The PDDBI was standardized with a sample of caregivers and teachers of children with ASD from a range of racial, ethnic, and socioeconomic backgrounds. (Cohen I L, Sudhalter V. PDD Behavioral Inventory Professional Manual. Lutz, Fla. Psychological Assessment Resources Inc; 2005). The PDDBI was collected from each participant's primary caregiver at the baseline, 6- and 12-month visits, as well as remotely at 3 and 9 months post-baseline.

The Expressive One-Word Picture Vocabulary Test-4 (EOWPVT-4) (Martin N A, Brownell R. EOWPVT-4. 4th ed. Novator, Calif. Academic Therapy Publication Inc; 2011) is a clinician-administered assessment which measures an individual's ability to match a spoken word with an image of an object, action, or concept. The EOWPVT-4 was administered to each child at the baseline and 6- and 12-month visits.

A task-designed to measure visual attention to social versus nonsocial stimuli via eye gaze tracking (EGT) was administered. EGT is a technology that enables quantification of gaze patterns of individuals from infancy through adulthood. The EGT hardware (Tobii TX300. Danderyd, Sweden: Tobii Technology; 2014) employs infrared light-emitting diodes and infrared cameras to measure corneal reflections, which are used to calculate eye gaze direction. During the EGT task, participants watched a 4-minute video of dynamic social stimuli, which includes episodes of an actress presenting bids for joint attention (Chawarska K, et al. *J Child Psychol Psychiatry* 2012; 53:903-913). Using these stimuli, prior studies have found that young children with ASD show decreased attention both to the entire scene, and to the actress' face during bids for joint attention. Decreased attention to the entire scene was also correlated with autism symptom severity (Chawarska K. et al. *J Child Psychol Psychiatry* 2012; 53:903-913). The EGT task was presented to each child at the baseline, 6- and 12-month visits.

Information about the number of hours that children were involved in behavioral, speech-language, occupational, and other behavioral therapies and educational services the child received was assessed every three months from baseline to 12 months post-baseline via a structured Intervention History Interview with the parent.

Statistical Methods

The analysis relied primarily on descriptive methods, beginning with a summary of the baseline characteristics of the cohort. Box plots were prepared to illustrate the distribution of continuous outcome measures over time. The frequency of ordinal outcome measures at each time point was plotted using bar charts. Statistical significance of change on continuous and ordinal outcomes was assessed using the Wilcoxon signed rank test except for the PDDBI, which was modeled using a fixed effect linear spline with knot at 3 months. This model was chosen over other longitudinal fixed and random effects models using the Akaike Information Criteria (AIC). EGT was analyzed using Generalized Estimating Equations (GEE) with logit link, binomial error structure, and exchangeable or unstructured working correlation. The association of baseline age, non-verbal IQ, and infused cell dose with change over time was explored in each analysis. There were not enough females enrolled to explore patterns of change by sex. Finally, we evaluated the potential for false-positive results by applying the Benjamini-Hochberg False Discovery Rate (FDR) procedure to the observed result for the baseline-to-6-month and 6-to-12-month follow-up periods.

Results

Characteristics of Study Participants and Autologous Cord Blood Units

Twenty-five (25) participants were enrolled in the study to receive an initial infusion of autologous cord blood (n=25). Of the 25 participants, 21 were males and the majority were Caucasian (n=23), with 1 Asian and 2 participants of mixed race. The median age of participants was 4.62 years (range 2.26-5.97), with a median nonverbal IQ of 65 (range 22-123). The median ADDS comparison score of the participants at study entry was 8.0 (range 6-10), and 72% had Moderately Severe or Severe ASD symptoms (Table 1). All participants completed the baseline and 6-month assessments. Three participants did not complete the 12-month assessment.

TABLE 1

Baseline characteristics of patients and autologous cord blood units (n = 25)

| Patient Characteristics | |
|---|---|
| Sex - no. (%) | |
| Female | 4 (16.0%) |
| Male | 21 (84.0%) |
| Age, years - median (range) | 4.62 (2.26-5.97) |
| Race - no. (%) | |
| Caucasian | 22 (88%) |
| Other | 3 (12%) |
| Ethnicity - no. (%) | |
| Hispanic | 2 (8%) |
| Not Hispanic | 23 (92%) |
| ADOS Severity Score - median (range) | 8 (6-10) |
| Non-verbal IQ - median (range) | 65 (22-123) |
| CGI-S - no. (%) | |
| Barely evident | 4 (16.0%) |
| Moderate ASD symptoms | 3 (12.0%) |
| Moderately severe ASD | 10 (40.0%) |
| Severe ASD symptoms | 8 (32.0%) |
| Cord Blood Characteristics - median (range) | |
| Total Cells Infused (TNCC), $\times 10^8$ | 4.42 (1.53-12.28) |
| Cell Dose Infused, $\times 10^6$/kg | 25.80 (9.97-80.80) |
| Viable CD34+ Dose Infused, $\times 10^6$/kg | 0.3 (0.1-4.2) |
| CFU Dose Infused, /kg | 1,225.50 (85.50-4,620.00) |

Abbreviations:
ADOS: Autism Diagnosis Observation Schedule;
CGI-S: Clinical Global Impression - Severity;
ASD: Autism Spectrum Disorder;
TNCC: Total Nucleated Cell Count;
CFU: Colony Forming Units Umbilical Cord Blood Infusions Autologous umbilical cord blood units were retrieved from two U.S. family cord blood banks, and one public bank (n=1). All were stored in dual compartment bags. To achieve the target cell dose of $1\text{-}5 \times 10^7$ TNC/kg, the entire cord blood unit was utilized in six (6) participants. In 19 participants, the 80% compartment of the cord blood unit was thawed and used for infusion and the remaining 20% portion was maintained in the cryopreserved state and stored, with the parents' permission, for potential future use. All patients completed their cord blood infusion. Characteristics of the thawed cord blood product administered to the patient are shown in Table 1. The median TNCC and viable CD34 cell doses infused were $2.6 \times 10^7$/kg (range $1\text{-}8 \times 10^7$) and $0.3 \times 10^5$/kg (range $0.1\text{-}4.2 \times 10^5$), respectively. The median CFUs infused was 1225.5/kg (range 85.5-4620). Although the dosing criteria utilized in this study were consistent with our previous studies utilizing privately banked cord blood units, these TNCC, CD34, and CFU values are lower than our prior experience. (Sun J, et al. *Transfusion* 2010; 50:1980-1987). Despite negative pre-cryopreservation sterility cultures reported by the bank, one unit grew coagulase negative staphylococcus from a post-thaw sample at Duke.

Safety of Autologous Cord Blood Infusions

Figure 1:
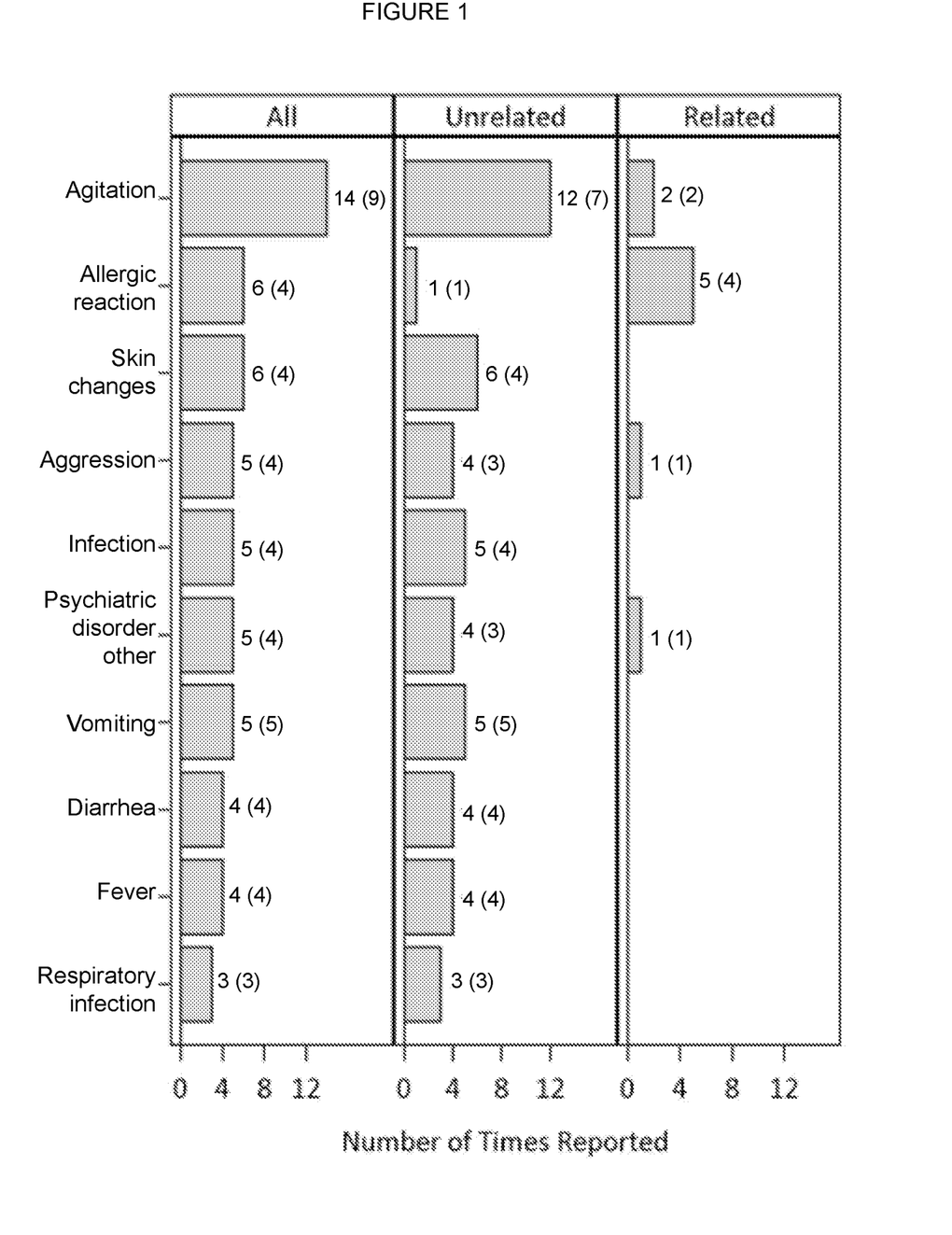
FIG. 1 illustrates the safety of autologous cord blood infusion in children with neurological disorders by assessing the frequency of Adverse Events (AEs), including both AEs related to the infusion and AEs unrelated to the infusion. No Serious AEs were reported in any participant. A total of 92 AEs were reported in 23 participants with a median of 3 events per participant (range: 1-15). The number of patients reporting an event is listed in parenthesis next to the frequency. All events were graded as Mild (71 events) or Moderate (21 events).

The primary endpoint of this open label phase I trial was safety (FIG. 1). As previously reported in our prior safety study of autologous cord blood infusion in children with neurological disorders (Sun J, et al. *Transfusion* 2010; 50:1980-1987), autologous cord blood infusion was well-tolerated. There were no Serious AEs reported in any participant. A total of 92 AEs were reported in 23 participants (FIG. 1) with a median of 3 events per participant (range: 1-15). All events were graded as Mild (71 events) or Moderate (21 events). Twelve events (13%) were considered related to the infusion, with the most common being Allergic Reaction, manifested by urticartia and/or cough occurring on the day of infusion (5 events in 4 participants; all Mild; 2 requiring an additional dose of IV Benadryl). The most common unrelated AEs were Agitation, Skin Changes, and typical childhood infections, reported between 2 days and 1 year post-infusion. There were no infusion-related infections or bloodstream or serious infections noted in any patient.

Behavioral Testing

Feasibility of administration was also tested and results of several measures typically used to assess behavioral outcomes in children with ASD were described. Multiple parent-rated and clinician-rated measures were evaluated. Behavioral outcomes correlated with baseline IQ, but not age or cell dose. Changes in behavior were also not correlated with the number of hours of behavioral interventions, speech-language therapy, occupational therapy or educational hours the child received during the tenure of the study. The measures chosen, a primary and key secondary behavioral endpoints (VABS-II, CGI-S, CGI-I, PDDBI, EOW-PBT), and the EGT biomarker measure all demonstrated improvements and are described below.

Figure 2:
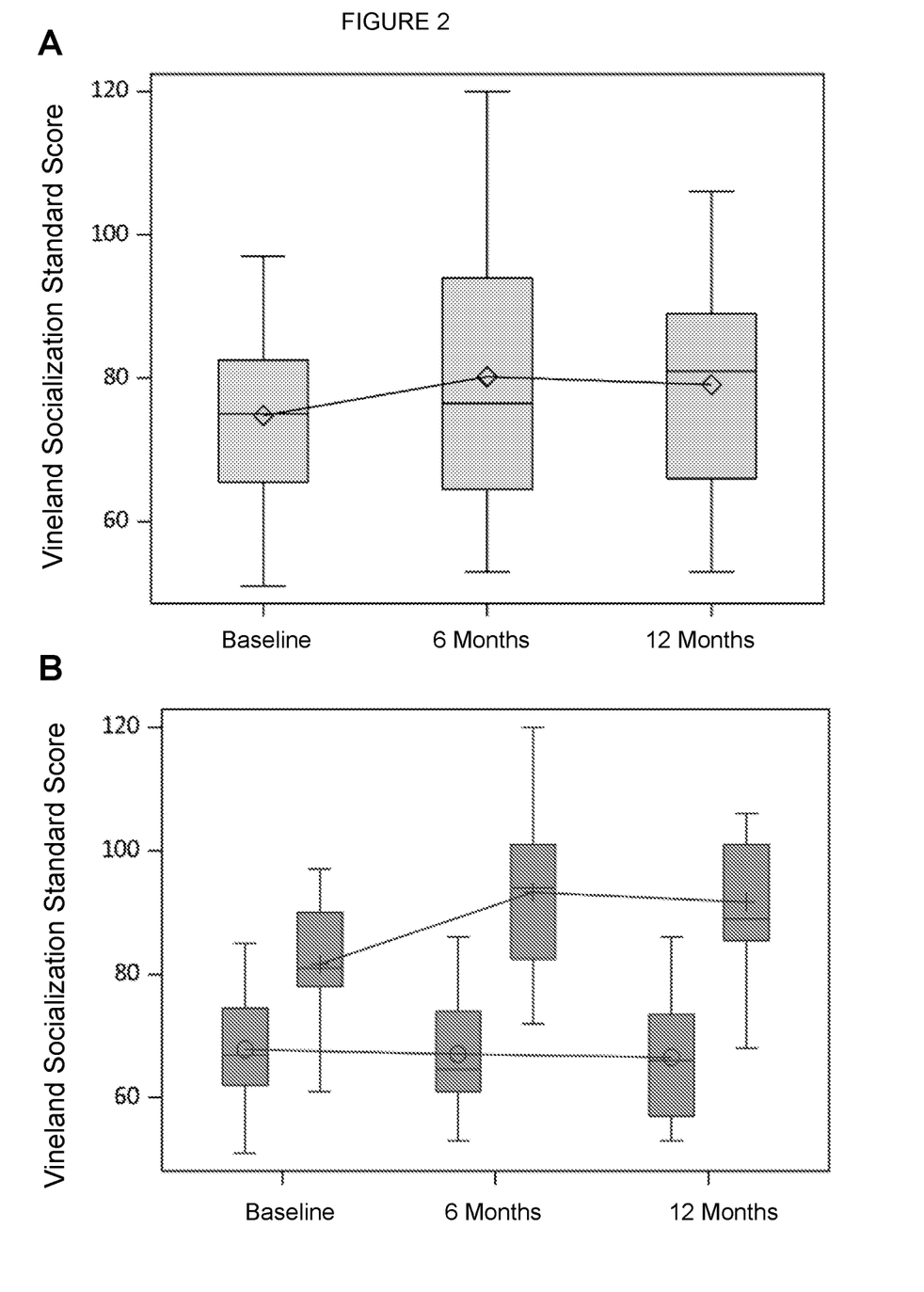

The VABS-II is parent-report measure that assesses socialization, communication and adaptive behaviors. FIG. 2 shows the distribution of standard scores in all patients (Panel A) and stratified by IQ (Panel B) for the VABS-II Socialization domain in the 24 participants who completed the assessments at all three time points. A statistically significant increase in standard score was observed from baseline to 6 months. This change was stable from 6-12 months. Change was positively correlated with nonverbal IQ in the Socialization ($r_s$=0.57, 95% CI: 0.20-0.79, P=0.004) and Adaptive Behavior ($r_s$=0.42, 95% CI: 0.01-0.70, P=0.04) domains, but not in the Communication domain ($r_s$=0.22, 95% CI: −0.21-0.57, P=0.31).

Figure 3:
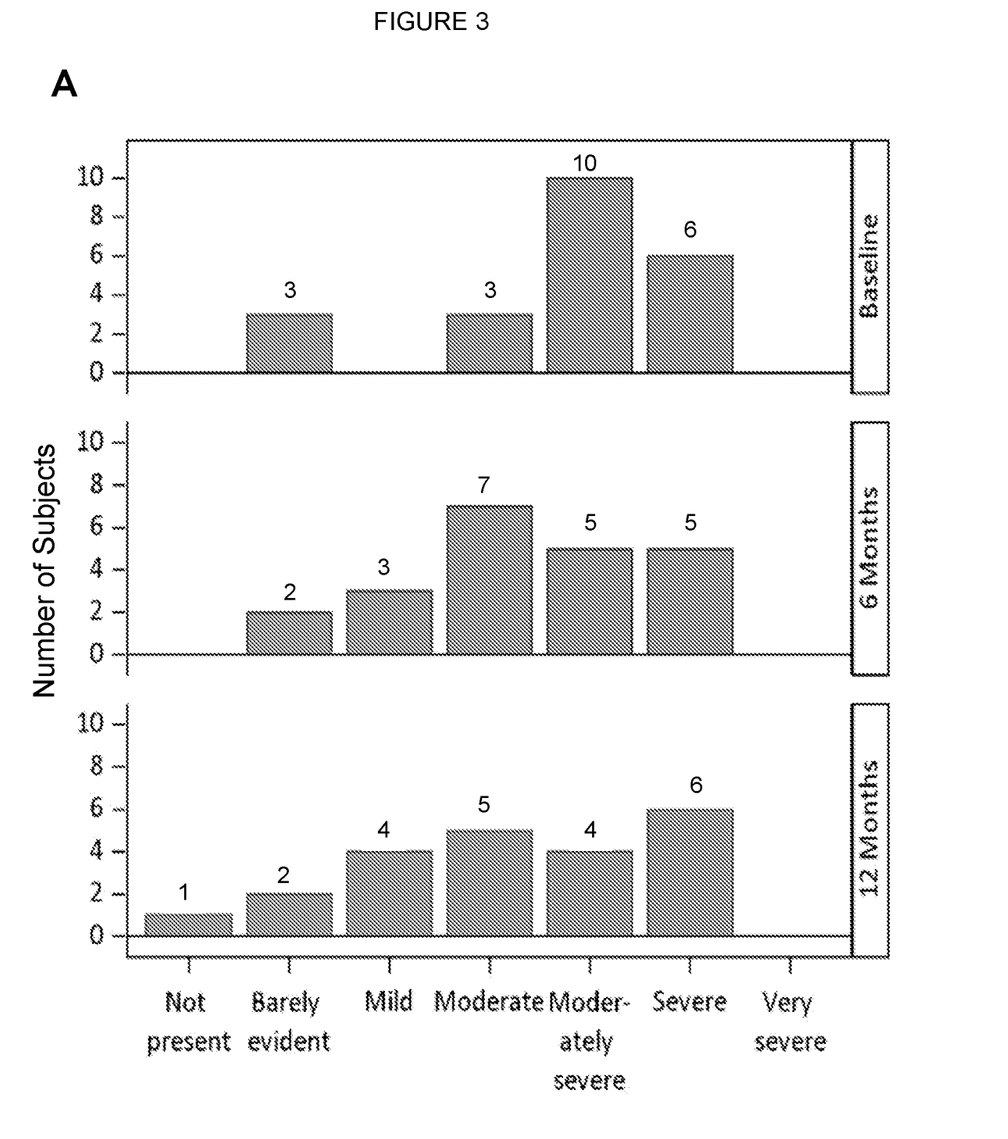

The CGI-S and CGI-I are clinician-rated measures used to assess the severity and change in severity of the core symptoms of ASD over time. FIG. 3 shows that distribution of CGI-S (Panel A) and CGI-I (Panel B) in 22 participants who were fully evaluable at all time points. In the CGI-S, at baseline, the majority of participants were classified as Moderately Severe (43.5%) or Severe (26.1%), and the remaining participants had Moderate or Barely Evident ASD symptoms (13.6% each). At 6 months, the proportion of participants with Moderately Severe and Severe symptoms decreased (22.7% each), with the remaining participants classified as Moderate (31.8%), Mild (13.6%), or Barely Evident (9.1%). FIG. 3B shows the distribution of CGI-I at 6 and 12 months. The improvement measured at each of these time points is relatev to baseline. At 6 months, 9 participants (40.9%) had not exhibited any change, whereas 2 (9.1%) were Minimally Improved, 8 (36.4%) were Much Improved and 3 (13.6%) were Very Much Improved (P<0.001). The CGI-I at 12 months was similar (P=0.001), although 2 participants (13.6%) were rated as Minimally Worse than baseline, whereas no participants were in the category at the 6-month assessments. The CGI-I at 12 months was associated with nonverbal IQ, but not age or infused cell dose (not shown).

The PDDBI—Autism Composite T-Score is a parent reported measure assessing ASD symptoms. The PDDBI was administered at baseline, 3, 6, 9, and 12 months (Table 2). The Autism Composite T-Score declined over time, suggesting an improvement in ASD symptoms. The majority of the change occurred in the interval from baseline to 3 months, with a predicted mean decline of 7.52 points (95% CI: −12.38, −2.67; P=0.004). There was no significant change from 3 to 12 months (mean: 0.72, 95% CI: −1.14, 2.57; P=0.43).

TABLE 2

Summary of behavioral assessments

| Outcome Measure | # of patients evaluated | Baseline to 6 Months | | 6 to 12 Months | |
|---|---|---|---|---|---|
| | | Change Score Median (Range) | P-value | Change Score Median (Range) | P-value [a] |
| VABS Socialization standard score | 24 | 2.0 (−8, 30) | 0.016 | 0 (−19, 9) | 0.602 |
| VABS Communication standard score | 24 | 4.5 (−8, 20) | 0.002 | 0.0 (−13, 13) | 0.459 |
| VABS Adaptive behavior composite standard score | 24 | 3 (−3, 24) | 0.007 | 0 (−12, 8) | 0.687 |
| VABS Motor standard score | 24 | 0 (−10, 7) | 0.788 | 0 (−14, 16) | 0.991 |
| VABS Daily living standard score | 24 | 1 (−9, 34) | 0.457 | 0 (−16, 16) | 0.999 |
| EOWPVT Raw score | 24 | 4 (−1, 24) | <0.001 | 5.5 (−12, 16) | 0.001 |
| PDDBI Autism Composite Score[b] | 24 | 7.53 (−12.38, −2.67) | 0.004 | 0.72 (−1.14, 2.57) | 0.430 |

[a] P-values are from the Wilcoxon signed rank test or spline model for PDD-BI
[b] The PDD-BI was collected at baseline, 3, and 6 months. Change scores are the predicted mean (and 95% confidence interval) from a linear spline model with knot at 3 months
Abbreviations:
VABS: Vineland Adaptive Behavior Scales-II;
EOWPVT: Expressive One-Word Picture Vocabulary Test-4;
PDDBI: Pervasive Developmental Disorder Behavior Inventory The EOWPVT is a clinician-administered assessment of the ability to match a spoken word with a picture. The EOWPVT raw score improved in 56% of patients between baseline and 6 months and in 68% of patients between 6-12 months (Table 2). Change in the EOWPVT raw score was associated with nonverbal IQ (baseline to 6 months: $r_s$=0.59, 95% CI: 0.23, 0.80, P=0.003; 6-12 months: $r_s$=0.55, 95% CI: 0.15, 0.78, P=0.009), but not age or infused cell dose (P>0.05 for all).

Eye-Gaze Tracking is a computerized test where the participants' eye movements are tracked by a computer while the subject views a naturalistic, dynamic social stimulus (actress making bids for engagement) surrounded by various nonsocial stimuli on a monitor. Attention was measured toward 4 targets (actress' eyes, mouth, face and upper body) and separate GEE models were fit for each target. Each model included 21 participants who were measured at baseline, 6, and 12 months. These models showed a 20% increase in odds of gazing at the actress' eyes over time (OR=1.20, 95% CI: 1.00, 1.43; P=0.048). There were no significant changes in gaze at the other 3 targets (Table 3). Examination of the relation between eye-tracking and the VABS-II Socialization Standard Score revealed that a 7-point change in VABS-II socialization standard score was associated with a 14% increase in odds of gazing at the actress (OR=1.14, 95% CI: 1.7, 1.21; P<0.001).

TABLE 3

Summary of Eye Tracking Studies (n = 21)

| Target | Odds Ratio (95% CI)[a] | P-value |
|---|---|---|
| Eyes | 1.20 (1.00, 1.43) | 0.048 |
| Actress | 1.02 (0.92, 1.12) | 0.716 |
| Mouth | 0.93 (0.81, 1.06) | 0.270 |
| Face | 1.02 (0.91, 1.14) | 0.800 |

[a]Odds ratio are estimated using Generalized Estimating Equations (one model for each target) and reflect the average trend in the cohort between successive 6-month follow-up periods (baseline to 6 months, and 6 to 12 months).

Adjustment for Multiple Testing

Given the large number of behavioral tests in this study, we explored the possibility of false positive results among the nine behavioral outcome measures by applying the False Discovery Rate method to the first and second 6-month follow-up periods separately (Table 4). All of the outcome measures that showed significant results during the first six months of follow-up remained statistically significant after FDR adjustment of P-values. During the period from 6 to 12 months, the EOWPVT and CGI-I remained statistically significant after application of the FDR procedure.

TABLE 4

Raw and Corrected P-values for Tests of the Null Hypothesis of No Change over Time in Behavioral Outcomes

| | Baseline to 6 Months | | 6 to 12 Months | |
|---|---|---|---|---|
| Outcome Measure | Raw P-value | FDR P-value | Raw P-value | FDR P-value |
| EOWPVT Raw Score | 0.0001 | 0.0009 | 0.0010 | 0.0059 |
| CGI-I | 0.0010 | 0.0045 | 0.0013 | 0.0059 |
| VABS Communication Standard Score | 0.0020 | 0.0060 | 0.3750 | 0.8262 |
| PDDBI Autism Composite T-Score[a] | 0.0040 | 0.0090 | 0.4300 | 0.8262 |
| VABS Adaptive Behavior Composite | 0.0070 | 0.0126 | 0.4590 | 0.8262 |
| VABS Socialization Standard Score | 0.0160 | 0.0240 | 0.6020 | 0.8833 |
| CGI-S | 0.0220 | 0.0283 | 0.6870 | 0.8833 |
| VABS Daily Living Standard Score | 0.4600 | 0.5175 | 0.9900 | 1.0000 |
| VABS Motor Function Standard Score | 0.7900 | 0.7900 | 1.0000 | 1.0000 |

[a]P-value for the PDDBI is for baseline to 3 months.
Abbreviations:
FDR: False Discovery Rate;
EOWPVT: Expressive One-Word Picture Vocabulary Test-4;
CGI-I/S: Clinical Global Impression - Improvement/Severity;
VABS: Vineland Adaptive Behavior Scales-II;
PDDBI: Pervasive Developmental Disorder Behavior Inventory Discussion In this phase I open-label study, the safety and feasibility of a single intravenous infusion of autologous umbilical cord blood in young children with ASD was evaluated. Changes in various behavioral and functional outcome measures were also described to determine which would be best suited for use as endpoints in future cell therapy trials. Assessments of adverse events over the 12 months post-infusion indicated that the cord blood infusion was safe and well tolerated. All related events were considered expected and resolved without sequelae. The most common unrelated AEs were agitation, skin changes, and typical childhood infections. Agitation, in particular, had not been a common side effect in our prior studies of autologous cord blood infusions in children with other acquired neurologic conditions, and thus may be specific to children with ASD. In this study, participants underwent sedation for an MRI immediately prior to their cord blood infusions. The increased incidence of agitation may thus reflect the challenges of waking from sedation and having an IV and pulse oximeter in place for a child with ASD, and as such may be related to their underlying condition.

Significant improvements in behavior were found across a wide range of outcome measures in this study. These included improvements in parent-reported measures including the VABS-II Socialization, Communication, and Adaptive Behavior Scores and the PDDBI, clinician assessments including the CGI-S, CGI-I, and EOWPVT, and objective eye gaze tracking measurements. Most of the observed behavioral changes occurred during the first six months and were sustained between six and 12 months post-inflation. A robust finding was that children's nonverbal IQ was correlated with change for the majority of outcomes measures, with higher nonverbal IQ being associated with greater improvements in behavior.

Of note, the majority of participants in this study were Caucasian, reflecting the demographic in the United States likely to have the resources and to choose to bank their baby's umbilical cord blood in a private bank. However, as ASD occurs in children of all demographic backgrounds, if cord blood therapy is effective then access would be limited to families with resources for private banking if only autologous cells are used. Accordingly, future studies will test the best available donor (autologous or allogeneic) versus placebo to lay the groundwork to extend access to this therapy for all affected children, if found to be effective.

While these results provide some promise for future work with cord blood-derived therapies in ASD, it is important to note the limitations of this study. As an uncontrolled open-label study, it is not possible to determine whether the observed behavioral changes were due to the treatment or reflect the natural course of development during the preschool period. Additionally, the small sample size makes it difficult to fully assess the contributions of confounding variables. While this study did not identify a correlation between behavioral changes and age, amount of behavioral intervention services or infused cell dose, the limited sample size and restricted age and dosing ranges may reduce the ability to detect such associations.

Each outcome measure described above showed sensitivity to change, indicating potential usefulness in larger trials. Furthermore, attrition due to noncompliance on these measures was minimal, suggesting that these measures are feasible with children with ASD in this age range. Using the results of this study as a guide, we selected the VABS Socialization Standard Score as the primary outcome measure for our next study with administration by trained clinicians to reduce parental expectancy effects. This score provides a validated measure of core social behaviors relevant to autism, showed sensitivity to change over a six-month period of time in the current study, and is feasible in a larger clinical trial. In keeping with recent draft guidance on design of autism clinical trials from the European Medicines Agency (ASD—Draft (2016) at http://www.ema.europa.eu/docs/en GB/document library/Scientific guideline/2016/03/WC500202650.pdf.), a single therapy may not improve all autism symptoms and global functional improvement is thus an important component of efficacy assessment in autism. Therefore, clinician-rated CGI and additional measures as secondary endpoints need to be further evaluated in a future phase II, double-blind randomized clinical trial designed to formally evaluate the efficacy of umbilical cord blood infusion in improving core symptoms of ASD.

The present disclosure demonstrates that intravenous infusion of autologous umbilical cord blood in young children with ASD is safe and feasible. The disclosure shows that the open-label, phase I trial in support of this conclusion describes significant improvements in behavior observed in the first six (6) months post-infusion and that these significant improvements were sustained at 12 months post-infusion. Higher baseline nonverbal IQ was associated with a greater degree of improvement. This disclosure identifies outcome measures that are feasible, sensitive to change, and developmentally-appropriate and, thus suitable for use to test the efficacy of cord blood therapy for the treatment of young children with ASD in future clinical trials and therapeutic settings.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A method of treating a patient suffering from an autism spectrum disorder, comprising administering to the patient a therapeutically effective amount of cord blood such that the disease is treated, wherein the amount of cord blood administered comprises $2.5 \times 10^7$ to about $2 \times 10^8$ cells/kg of body weight.

2. The method of claim 1, wherein the cord blood is administered systemically.

3. The method of claim 2, wherein the cord blood in administered by intravenous infusion.

4. The method claim 1, wherein the cord blood is autologous cord blood.

5. The method of claim 1, wherein the cord blood is administered in a single dose or in multiple doses.

6. A method of assessing the therapeutic effectiveness of cord blood treatment on a patient suffering from an autism spectrum disorder comprising:
   a. performing one or more appropriate behavioral and/or biomarker tests on the patient to establish behavioral and biomarker baseline score(s);
   b. administering an effective amount of cord blood to the patient, wherein the amount of cord blood administered comprises $2.5 \times 10^7$ to about $2 \times 10^8$ cells/kg of body weight;
   c. reevaluating the patient at one or more time points post-administration of cord blood by the same one or more behavioral and/or biomarker tests set forth in (a), to obtain one or more post-treatment scores; and
   d. comparing the results in (c) with the baseline score(s) established in (a), wherein an improved score in step (c), relative to the baseline score in step (a), indicates that the cord blood treatment was therapeutically effective.

7. The method of claim 6, wherein the behavioral test(s) performed in (a) and (c) comprise one or more of: Vineland Adaptive Behavior Scales-II (VABS-II), Clinical Global Impression Scale (CGI), Pervasive Developmental Disorder Behavior Inventory (PDDBI), Expressive One-Word Picture Vocabulary Test-4 (EOWPVT-4), Behavior Assessment for Children-Social Skills subscale, Aberrant Behavior Checklist, Sensory Experiences Questionnaire, Repetitive Behavior Scale, Intelligence Scales (Mullen Scales of Early Learning or Stanford-Binet), Language Environment Analysis, Preschool Age Psychiatric Assessment, Aberrant Behavior Checklist, ATN GI Symptoms Inventory, and Parenting Stress Index.

8. The method of claim 6, wherein the hiomarker test(s) performed in (a) and (c) comprise one or more of: Eye Gaze Tracking of Social Stimuli (EGT), Electroencephalogram (EEG), and brain Magnetic Resonance Imaging (MRI).

9. The method of claim 6, wherein reevaluation of the patient in (c) is performed at one or more time points comprising: 3 months, 6 months, 9 months, 12 months, 18 months, and 24 months post-administration.

10. The method of claim 4, wherein the cord blood is administered systemically.

11. The method of claim 10, wherein the cord blood is administered intravenous infusion.

12. The method of claim 4, wherein the cord blood is administered in a single dose or in multiple doses.

13. The method of claim 3, wherein the cord blood is administered in a single dose or in multiple doses.

14. The method of claim 7, wherein reevaluation of the patient in (c) is performed at one or more time points comprising: 3 months, 6 months, 9 months, 12 months, 18 months, and 24 months post-administration.

15. The method of claim 8, wherein reevaluation of the patient in (c) is performed at one or more time points comprising: 3 months, 6 months, 9 months, 12 months, 18 months, and 24 months post-administration.

* * * * *